(12) United States Patent
Takeuchi et al.

(10) Patent No.: US 9,214,753 B2
(45) Date of Patent: Dec. 15, 2015

(54) CONNECTOR FOR BIOLOGICAL INFORMATION MEASUREMENT, AND BIOLOGICAL INFORMATION MEASUREMENT DEVICE USING SAME

(71) Applicant: PANASONIC HEALTHCARE HOLDINGS CO., LTD., Minato-Ku, Tokyo (JP)

(72) Inventors: Yoshiki Takeuchi, Ehime (JP); Kaoru Shigematsu, Ehime (JP)

(73) Assignee: PANASONIC HEALTHCARE HOLDINGS CO., LTD., Minato-Ku, Tokyo (JP)

( * ) Notice: Subject to any disclaimer, the term of this patent is extended or adjusted under 35 U.S.C. 154(b) by 0 days.

(21) Appl. No.: 14/388,243

(22) PCT Filed: Jun. 4, 2013

(86) PCT No.: PCT/JP2013/003498
§ 371 (c)(1),
(2) Date: Sep. 26, 2014

(87) PCT Pub. No.: WO2013/183281
PCT Pub. Date: Dec. 12, 2013

(65) Prior Publication Data
US 2015/0280350 A1 Oct. 1, 2015

(30) Foreign Application Priority Data

Jun. 5, 2012 (JP) .................................. 2012-127641
Apr. 17, 2013 (JP) .................................. 2013-086342

(51) Int. Cl.
*G01D 11/24* (2006.01)
*H01R 13/504* (2006.01)
*G01N 33/487* (2006.01)

(52) U.S. Cl.
CPC ........ *H01R 13/504* (2013.01); *G01N 33/48785* (2013.01)

(58) Field of Classification Search
CPC ............................. G01D 11/24; G01D 11/245
USPC .............................................. 73/431
See application file for complete search history.

(56) References Cited

U.S. PATENT DOCUMENTS

| 6,616,819 B1 | 9/2003 | Liamos et al. |
| 6,749,740 B2 | 6/2004 | Liamos et al. |

(Continued)

FOREIGN PATENT DOCUMENTS

| JP | 2003-513279 A | 4/2003 |
| JP | 2006-511788 A | 4/2006 |

(Continued)

OTHER PUBLICATIONS

The Search Report from the corresponding International Patent Application No. PCT/JP2013/003498 issued on Jul. 9, 2013.

(Continued)

*Primary Examiner* — Lisa Caputo
*Assistant Examiner* — Jamel Williams
(74) *Attorney, Agent, or Firm* — Shinjyu Global IP (57) ABSTRACT

In the present invention, a metal upper cover that covers an upper face opening of a frame is mounted on this upper face opening, and a bent piece that is inserted into a bent piece insertion hole provided to the frame is provided to a portion of the upper face cover on the side of a sensor insertion hole. Furthermore, ground connection pieces formed by extending the outside of the left and right sides of the frame from the upper face toward the lower face are provided in portions opposite the left and right edges linked to the edge of the top cover on which the sensor insertion opening of the frame is provided.

19 Claims, 10 Drawing Sheets

(56) References Cited

U.S. PATENT DOCUMENTS

| | | |
|---|---|---|
| 6,942,518 B2 | 9/2005 | Liamos et al. |
| 6,946,299 B2 | 9/2005 | Neel et al. |
| 7,896,703 B2 | 3/2011 | Stafford et al. |
| 7,896,704 B2 | 3/2011 | Stafford et al. |
| 7,914,335 B2 | 3/2011 | Stafford et al. |
| 8,066,858 B2 | 11/2011 | Wang et al. |
| 8,377,272 B2 | 2/2013 | Kim et al. |
| 8,398,443 B2 | 3/2013 | Groll et al. |
| 2002/0053523 A1 | 5/2002 | Liamos et al. |
| 2002/0084196 A1 | 7/2002 | Liamos et al. |
| 2002/0148739 A2 | 10/2002 | Liamos et al. |
| 2002/0157948 A2 | 10/2002 | Liamos et al. |
| 2003/0203498 A1 | 10/2003 | Neel et al. |
| 2004/0094432 A1 | 5/2004 | Neel et al. |
| 2004/0094433 A1 | 5/2004 | Neel et al. |
| 2004/0099540 A1 | 5/2004 | Neel et al. |
| 2004/0104131 A1 | 6/2004 | Neel et al. |
| 2004/0182703 A1 | 9/2004 | Bell et al. |
| 2004/0225230 A1 | 11/2004 | Liamos et al. |
| 2005/0045476 A1 | 3/2005 | Neel et al. |
| 2007/0089987 A1 | 4/2007 | Neel et al. |
| 2007/0249921 A1 | 10/2007 | Groll et al. |
| 2008/0001128 A1 | 1/2008 | Goldberg |
| 2008/0283396 A1 | 11/2008 | Wang et al. |
| 2009/0108013 A1 | 4/2009 | Van Der Velde et al. |
| 2009/0260985 A1 | 10/2009 | Wang et al. |
| 2009/0260986 A1 | 10/2009 | Wang et al. |
| 2010/0015860 A1 | 1/2010 | Stafford et al. |
| 2010/0032321 A1 | 2/2010 | Kim et al. |
| 2010/0064800 A1 | 3/2010 | Stafford et al. |
| 2010/0065426 A1 | 3/2010 | Stafford et al. |
| 2010/0126884 A1 | 5/2010 | Wang et al. |
| 2010/0315106 A1 | 12/2010 | Stafford et al. |
| 2011/0184264 A1 | 7/2011 | Galasso et al. |
| 2015/0014159 A1* | 1/2015 | Takeuchi ............. G01N 27/327 204/403.01 |
| 2015/0136818 A1* | 5/2015 | Tanizaki .......... G01N 33/48785 224/191 |

FOREIGN PATENT DOCUMENTS

| | | |
|---|---|---|
| JP | 2006-286601 A | 10/2006 |
| JP | 2009-178367 A | 8/2009 |
| JP | 2009-534635 A | 9/2009 |
| JP | 2010-520463 A | 6/2010 |
| JP | 2011-502255 A | 1/2011 |
| JP | 2011-528437 A | 11/2011 |
| JP | 2012-18930 A | 1/2012 |
| JP | 4993854 B2 | 8/2012 |
| JP | 5031024 B2 | 9/2012 |
| JP | 5181400 B2 | 4/2013 |
| JP | 2013-518288 A | 5/2013 |
| JP | 5203395 B2 | 6/2013 |
| WO | 2011/094315 A1 | 8/2011 |

OTHER PUBLICATIONS

Office Action from the corresponding Japanese Patent Application No. 2014-519837 issued on Sep. 15, 2015.

* cited by examiner

CONNECTOR FOR BIOLOGICAL INFORMATION MEASUREMENT, AND BIOLOGICAL INFORMATION MEASUREMENT DEVICE USING SAME

PRIORITY

This application claims priority to International Application PCT/JP2013/003498, with an international filing date of Jun. 4, 2013 which claims priority to Japanese Patent Application No. 2012-127641 filed on Jun. 5, 2012 and Japanese patent Application No. 2013-086342 filed on Apr. 17, 2013. The entire disclosures of International Application PCT/JP2013/003498, Japanese Patent Application No. 2012-127641, and Japanese patent Application No. 2013-086342 are hereby incorporated herein by reference.

TECHNICAL FIELD

The present invention relates to a connector for biological information measurement, in which biological information such as a blood glucose level is measured from blood, for example, and to a biological information measurement device in which this connector is used.

BACKGROUND

A conventional biological information measurement device of this type comprised a main body case having a sensor mounting component, and a connector for biological information measurement that was provided to the inside of the sensor mounting component of this main body case.

Also, a connector for biological information measurement has a square frame that is molded from resin and has an upper face opening and a lower face opening. A connection terminal, the rear end of which is pulled outside of the frame, the middle part of which is embedded in the frame, and the front end of which is disposed on the inside of the frame, is provided between the upper face opening and the lower face opening on a first edge of this frame. There is further provided a sensor insertion port between the upper face opening and the lower face opening of a second edge opposite the first edge of the frame. The connector for biological information measurement is mounted on a connection substrate inside the main body case (see Patent Literature 1: JP 2003-513279, for example).

If a sensor is inserted from the sensor mounting component provided to the main body case of this biological information measurement device, the sensor is electrically connected to the connection terminal of the connector for biological information measurement provided to the inside of the main body case.

With this connector for biological information measurement, the connection terminal is molded integrally with the frame, which is molded from a synthetic resin. The frame has an upper face opening and a lower face opening in order to position the connection terminal in the resin molding of the frame, and in order to hold the connection terminal in the mold from above and below, since the front end of the connection terminal is not embedded in the resin.

However, if there is an upper face opening in the frame, foreign matter may go through the upper face opening and reach the connection terminal portion when this connector for biological information measurement is being stored, or during mounting of the biological information measurement device on the connection substrate. As a result, there is the risk of defective connection between the connection terminal and the sensor.

SUMMARY

The present invention comprises square frame that is molded from resin and has an upper face opening and a lower face opening, and a connection terminal that is provided between the upper face opening and the lower face opening on a first edge of the frame, the rear end of which is pulled outside of the frame, the middle part of which is embedded in the frame, and the front end of which is disposed on the inside of the frame. Also comprised is a sensor insertion port that is provided between the upper face opening and the lower face opening on a second edge of the frame opposite the first edge. A metal upper cover that covers the upper face opening is mounted on the upper face opening of the frame, a bent piece that is inserted into a bent piece insertion hole provided to the second edge of the frame is provided to a portion of the upper face cover on the side of the sensor insertion port, and ground connection pieces formed by extending the outside of the left and right sides of the frame from the upper face toward the lower face are provided in portions of the upper face cover opposite the left and right edges of the frame.

With the present invention, since the metal upper face cover is mounted to cover the upper face opening, no foreign matter will get through the upper face opening and reach the connection terminal portion when this connector for biological information measurement is being stored, or during mounting of the biological information measurement device on the connection substrate. As a result, defective connection between the connection terminal and the sensor can be prevented.

Furthermore, with the present invention, a bent piece that is inserted into a bent piece insertion hole provided to the second edge of the frame is provided to a portion of the upper face cover on the side of the sensor insertion port, and ground connection pieces formed by extending the outside of the left and right sides of the frame from the upper face toward the lower face are provided in portions opposite the left and right edges of the frame, so damage that would be caused by static electricity can be prevented.

That is, when biological information is to be measured, a sensor is inserted through the sensor insertion port into the frame, after which it is connected to the connection terminal, but if the person holding this sensor is charged at a high voltage, it is possible that static electricity could flow through the sensor to the connection terminal, or to a measurement component or the like connected to the connection terminal. There is therefore a risk of damage to the measurement component or the like.

With the present invention, however, a bent piece that is inserted into a bent piece insertion hole provided to the second edge of the frame is provided to a portion of the upper face cover on the sensor insertion port side, and ground connection pieces formed by extending the outside of the left and right sides of the frame from the upper face toward the lower face are provided in portions opposite the left and right edges linking the first edge and the second edge of the frame. Therefore, when a sensor is inserted in the sensor insertion port, high-voltage static electricity will flow from the bent piece insertion hole portion of the frame, through the bent piece of the upper face cover inserted into this bent piece insertion hole, and to the ground connection pieces of the upper face cover.

As a result, no static electricity will flow through the sensor to the connection terminal, or to a measurement component or the like connected to the connection terminal, so this prevents damage to the various components.

DETAILED DESCRIPTION

An embodiment of the present invention will now be described through reference to the appended drawings, but the configuration of the present invention is not limited by the following embodiments.

First Embodiment

Figure 1:
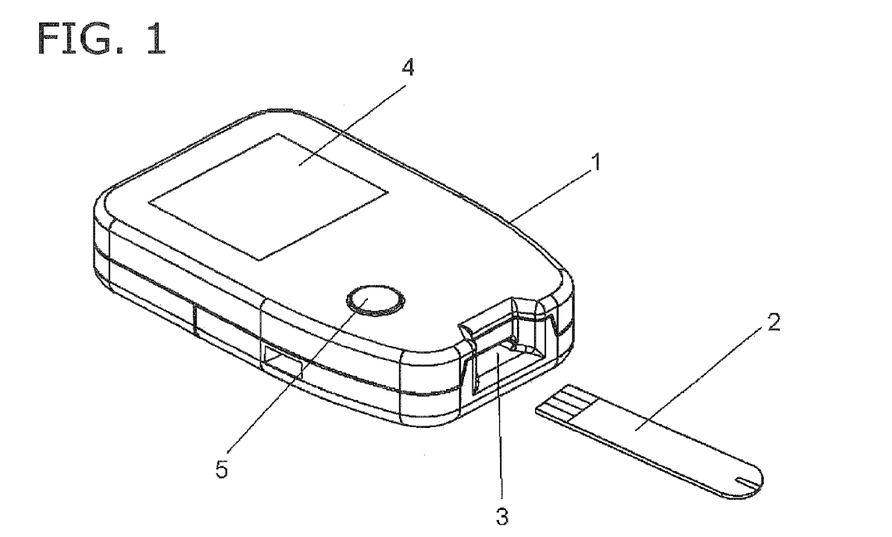
FIG. 1 is an oblique view of the biological information measurement device in a first embodiment of the present invention.

In FIG. 1, the main body case 1 of a measurement device for measuring blood glucose levels, which is an example of a biological information measurement device, is formed in a substantially cuboid shape. A sensor mounting component 3 into which is inserted a blood glucose level sensor 2, which is an example of a biological information measurement sensor, is provided at one end of the main body case 1. A display component 4 and a power switch 5 are provided to the upper face of the main body case 1.

Figure 2:
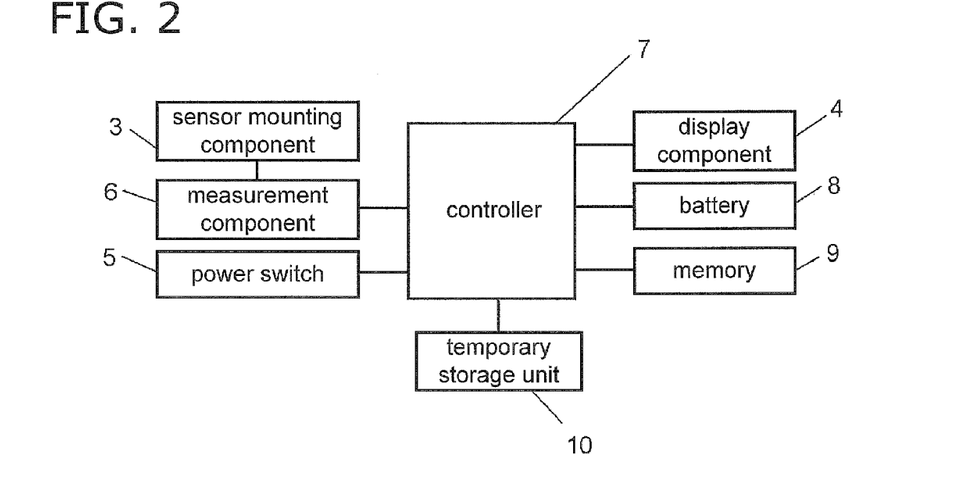
FIG. 2 is a block diagram of the biological information measurement device in the first embodiment of the present invention.

As shown in FIG. 2, a measurement component 6 that is electrically connected to the sensor mounting component 3, and a controller 7 that is connected to this measurement component 6 are disposed in the interior of the main body case 1. The display component 4, the power switch 5, and a battery 8 are connected to this controller 7, and a memory 9 consisting of a ROM that stores control programs for this controller 7 is also connected. The measurement procedure used by the measurement component 6 is also stored in this memory 9. The controller 7 is connected to a temporary storage unit 10 that temporarily stores work performed by the controller 7.

Figure 3:
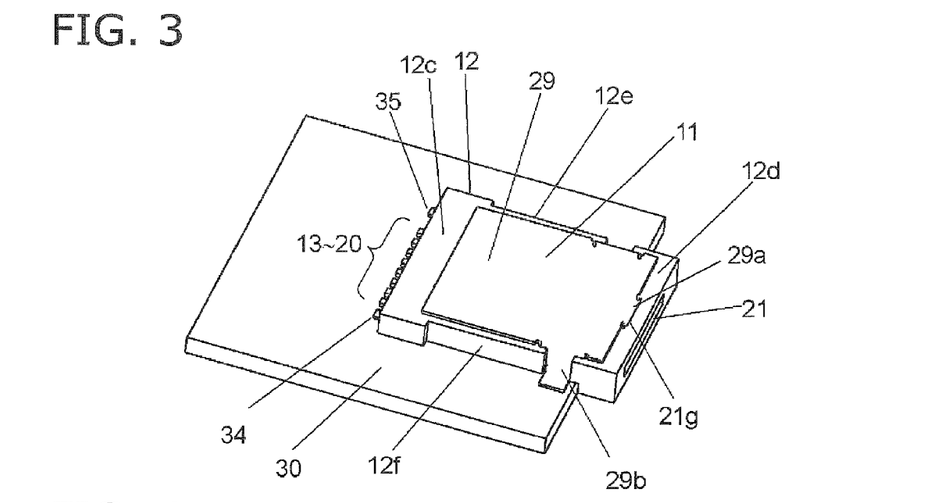
FIG. 3 is an oblique view of the connector for biological information measurement used in the biological information measurement device in the first embodiment of the present invention.
Figure 4:
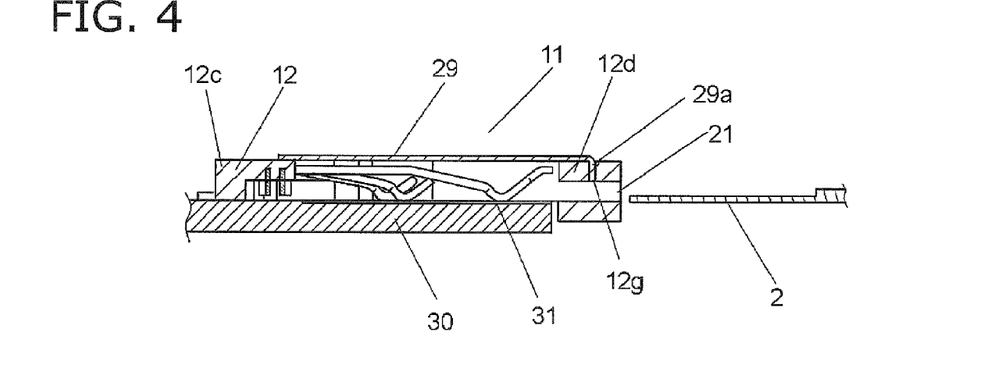
FIG. 4 is a cross section of the connector for biological information measurement in the first embodiment of the present invention.
Figure 5:
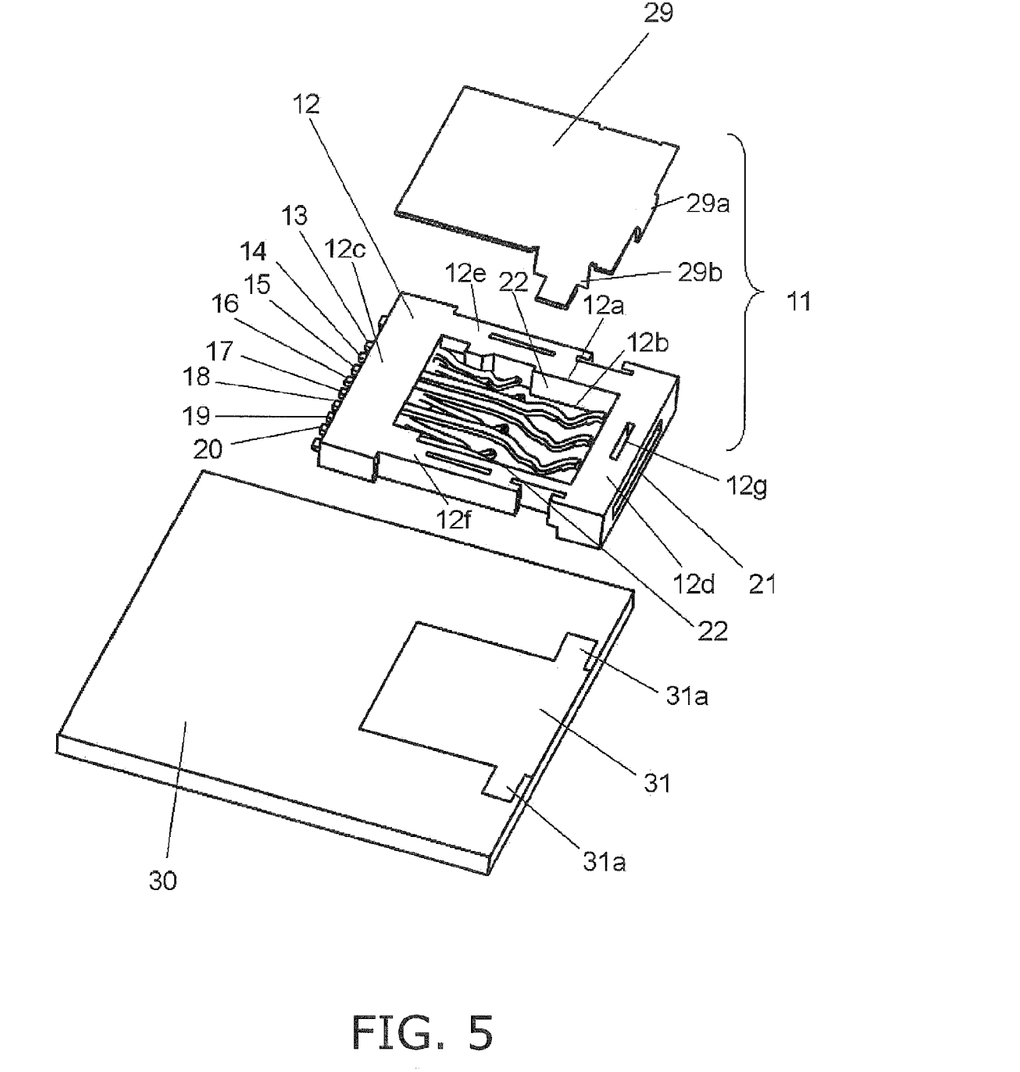
FIG. 5 is an exploded oblique view of the connector for biological information measurement in the first embodiment of the present invention.

The connector 11 for biological information measurement shown in FIGS. 3 to 5 is disposed to the rear of the sensor mounting component 3 inside the main body case 1.

As shown in FIG. 5, this biological information measurement connector 11 has a square frame 12 which is formed from a synthetic resin and has a rectangular upper face opening 12a and a rectangular lower face opening 12b. A plurality of connection terminals 13 to 20, the rear ends of which are pulled outside of the frame 12, the middle parts of which are embedded in the frame 12, and the front ends of which are disposed on the inside of the frame 12, are provided between the upper face opening 12a and the lower face opening 12b on a first edge 12c of the frame 12.

The biological information measurement connector 11 further comprises a sensor insertion port 21 that is wider than it is tall, between the upper face opening 12a and the lower face opening 12b on a second edge 12d that is opposite the first edge 12c of the frame 12. This sensor insertion port 21 is in the form of a through-hole that is wider than it is tall, in order to insert the flat blood glucose level sensor 2 and to prevent water and dirt from getting in.

As shown in FIG. 5, the middle part of the frame 12 passes through from the rectangular upper face opening 12a to the rectangular lower face opening 12b, and a thin, flat space is formed here. The upper face opening 12a and the lower face opening 12b are utilized to mold the frame 12 integrally with the sensor insertion port 21 and the connection terminals 13 to 20 in upper and lower molds (not shown).

More specifically, the connection terminals 13 to 20 are disposed in the lower mold (not shown) so that they are spaced apart a specific distance in the horizontal direction, and are then covered with the upper mold (not shown), and in this state a synthetic resin is injected into the upper and lower molds to integrally mold the frame 12 shown in FIGS. 3 to 5.

That is, for the connection terminals 13 to 20 and the frame 12 to be molded integrally, it is necessary to use the square frame 12 having the upper face opening 12a and the lower face opening 12b.

In a state in which the connection terminals 13 to 20 are spaced a specific distance apart on the first edge 12c of the frame 12 thus formed, the middle parts thereof are embedded on the first edge 12c of the frame 12. The rear ends of the connection terminals 13 to 20 here are pulled out to the outside of the first edge 12c of the frame 12, and the front ends are pulled out to the inside of the frame 12.

With the frame 12 in which the connection terminals 13 to 20 and the sensor insertion port 21 are integrally molded, the second edge 12d where the sensor insertion port 21 is provided is connected to the left and right edges 12e and 12f of the frame 12 at positions on the left and right of the sensor insertion port 21. The left and right edges 12e and 12f of the frame 12 are such that their inner face sides between the upper face opening 12a and the lower face opening 12b serve as sensor insertion guide faces 22.

Figure 6:
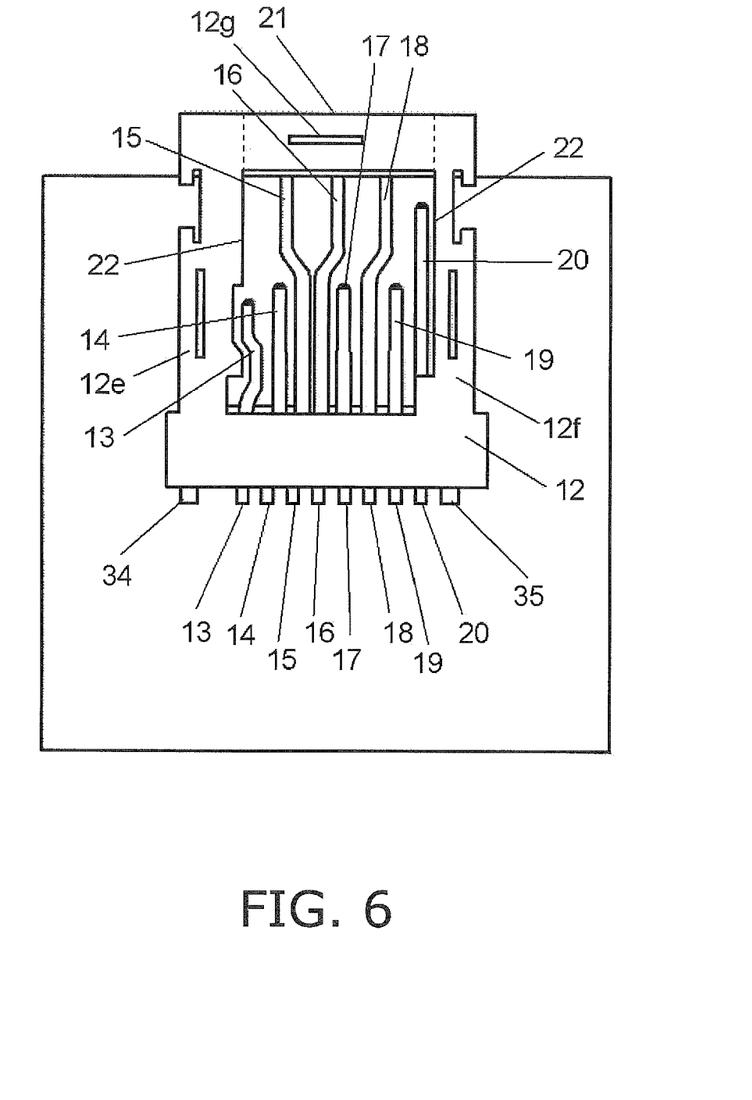
FIG. 6 is a plan view of the connector for biological information measurement in the first embodiment of the present invention.

As shown in FIG. 6, these sensor insertion guide faces 22 are the same width as the sensor insertion port 21. That is, when the rear end side of the blood glucose level sensor 2 in FIG. 1 is inserted through the sensor insertion port 21, the left and right long edges of the blood glucose level sensor 2 will be guided to the rear by the left and right sensor insertion guide faces 22.

Figure 8:
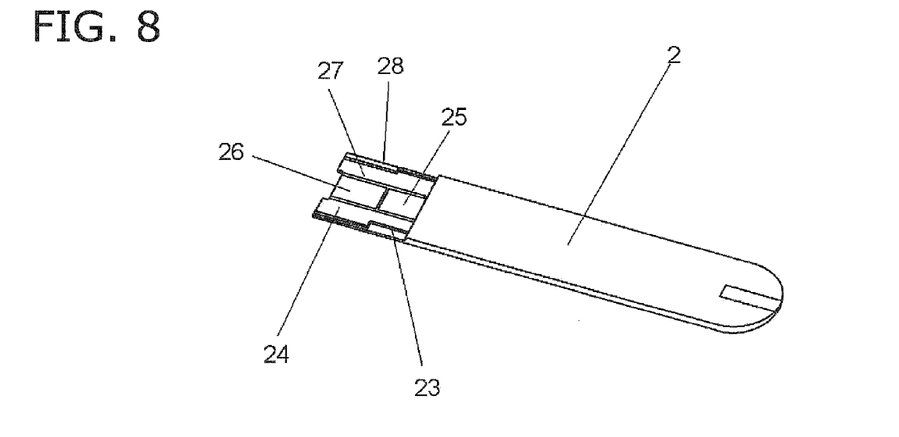
FIG. 8 is an oblique view of a sensor inserted into the connector for biological information measurement in the first embodiment of the present invention.

As shown in FIG. 8, the blood glucose level sensor 2 comprises connection electrodes 23 to 28. Therefore, when the rear end side of the blood glucose level sensor 2 is inserted through the sensor insertion port 21, the connection electrode 23 is connected to the connection terminal 20 shown in FIG. 6, the rear end side of the connection electrode 24 is connected to the connection terminal 19, and the front end side of the connection electrode 24 is connected to the connection terminal 18.

The connection terminal 16 is connected to the connection electrode 25, and the connection terminal 17 is connected to the connection electrode 26. The connection terminal 14 is connected to the rear end side of the connection electrode 27, the connection terminal 15 is connected to the front end side of this connection electrode 27, and the connection terminal 13 is connected to the connection electrode 28.

What is important here, as shown in FIG. 8, is that the connection terminals 13 to 20 are suitably connected as discussed above to the plurality of connection electrodes 23 to 28 disposed in an adjacent state on the rear end side of the blood glucose level sensor 2.

In view of this, in this embodiment the sensor insertion port 21 is integrally provided to the frame 12 in which the connection terminals 13 to 20 have been integrated, and the sensor insertion guide faces 22 are provided on the left and right sides thereof. Accordingly, when the rear end side of the blood glucose level sensor 2 is inserted into the sensor insertion port 21, the rear end side of the blood glucose level sensor 2 is suitably guided rearward by the left and right sensor insertion guide faces 22.

As a result, the connection electrodes 23 to 28 of the blood glucose level sensor 2 can be properly connected to the connection terminals 13 to 20.

In the formation of the frame 12, the contact faces of the upper and lower molds are provided under the sensor insertion guide faces 22. That is, since lines that serve as parting lines are formed in the contact faces of the upper and lower molds, these parting lines are to be under the sensor insertion guide faces 22. The reason for this is so that the parting lines will not hit the left and right long edges of the blood glucose level sensor 2 during insertion of the blood glucose level sensor 2.

Specifically, when the blood glucose level sensor 2 is inserted rearward in a state in which its left and right long edges are touching these parting lines, the blood glucose level sensor 2 cannot be properly inserted even though the sensor insertion guide faces 22 have been provided. In view of this, the parting lines are disposed under the sensor insertion guide faces 22 as mentioned above.

When the frame 12 has the upper face opening 12a, foreign matter may get into the portions of the connection terminals 13 to 20 through the upper face opening 12a during storage of the biological information measurement connector 11, or when the biological information measurement connector 11 is mounted on a connection substrate 30 of the biological information measurement device. As a result, there is a risk that connection will be interrupted between the blood glucose level sensor 2 and the connection terminals 13 to 20.

In view of this, in this embodiment a metal upper face cover 29 that covers the entire upper face opening 12a is mounted to the upper face opening 12a of the frame 12 as shown in FIG. 5. Consequently, no foreign matter will get into the portions of the connection terminals 13 to 20 through the upper face opening 12a during storage of the biological information measurement connector 11, or when the biological information measurement connector 11 is mounted on the connection substrate 30 of the biological information measurement device. This prevents connection from being interrupted between the blood glucose level sensor 2 and the connection terminals 13 to 20.

Figure 9:
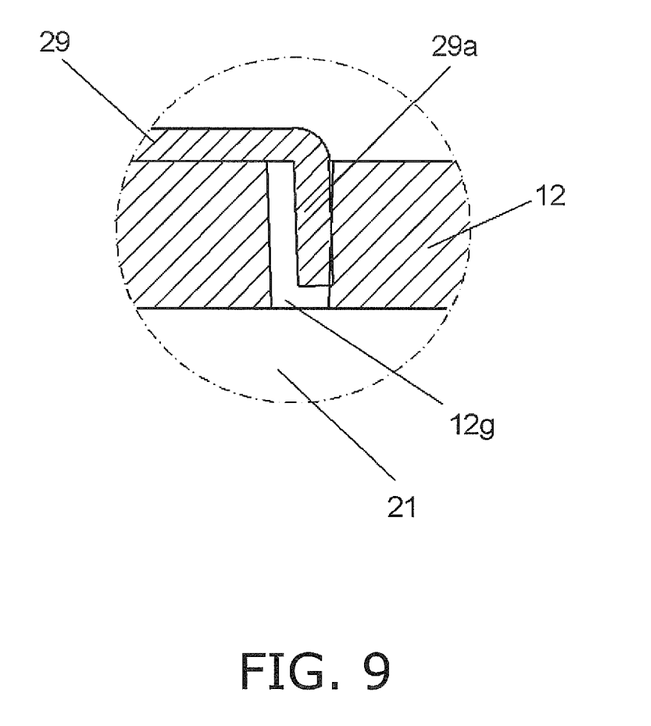
FIG. 9 is a cross section of the main components of the connector for biological information measurement in the first embodiment of the present invention.

As shown in FIGS. 4, 5, and 9, a bent piece 29a that is inserted into a bent piece insertion hole 12g provided to the second edge 12d of the frame 12 is provided on the sensor insertion port 21 side of the upper face cover 29. This bent piece 29a is formed by bending the end of the upper face cover 29 downward.

As shown in FIGS. 4 and 9, this bent piece 29a is inserted into the bent piece insertion hole 12g provided to the upper face of the sensor insertion port 21. The bent piece insertion hole 12g is provided on the upper face side of the sensor insertion port 21, which is wider than it is tall.

When the bent piece 29a formed by bending the upper face cover 29 is inserted into this bent piece insertion hole 12g, as shown in FIG. 9, the spring back of the bent piece 29a causes it to be pressed against the inner face of the bent piece insertion hole 12g, which is above the sensor insertion port 21.

As shown in FIG. 5, ground connection pieces 29b that extend from the upper face of the frame 12 toward the lower face and are bent down on the outside of the left and right edges 12e and 12f of the frame 12 are provided at opposite portions of the left and right edges 12e and 12f of the frame 12. These ground connection pieces 29b come into contact with ground patterns 31a that stick out to the left and right from a conductive pattern 31 on the connection substrate 30, and are then electrically and mechanically connected by a conductive adhesive agent.

Therefore, when the blood glucose level sensor 2 is inserted through the sensor insertion port 21 into the frame 12 in the measurement of biological information, the connection terminals 13 to 20, or the measurement component 6 or the like that is connected to the connection terminals 13 to 20, will not be damaged by static electricity.

That is, in the measurement of biological information, the blood glucose level sensor 2 is inserted through the sensor insertion port 21 into the frame 12, after which it is connected to the connection terminals 13 to 20. However, if the person holding the blood glucose level sensor 2 is charged at a high voltage, there is the risk that static electricity will flow through the blood glucose level sensor 2 to the connection terminals 13 to 20, or to the measurement component 6 or the like that is connected to the connection terminals 13 to 20, and damage these parts.

With this embodiment, however, the bent piece 29a that is inserted into the bent piece insertion hole 12g provided to the second edge 12d of the frame 12 is provided to the portion of the upper face cover 29 on the sensor insertion port 21 side. Furthermore, the ground connection pieces 29b that extend from the upper face of the frame 12 toward the lower face on the outside of the left and right edges 12e and 12f of the frame 12 are provided at opposite portions of the left and right edges 12e and 12f of the frame 12. Also, the ground connection pieces 29b are electrically and mechanically connected by a conductive adhesive agent to the ground patterns 31a that stick out on the left and right from the conductive pattern 31 of the connection substrate 30. The conductive pattern 31 is connected to a ground line.

Therefore, when the blood glucose level sensor 2 is inserted into the sensor insertion port 21, static electricity flows from the bent piece insertion hole 12g portion of the frame 12, through the bent piece 29a of the upper face cover 29 inserted into the bent piece insertion hole 12g, and to the ground connection pieces 29b of the upper face cover 29 and the ground patterns 31a. As a result, the static electricity does not flow through the blood glucose level sensor 2 to the connection terminals 13 to 20, or to the measurement component 6 or the like connected to the connection terminals 13 to 20, and this prevents damage to the various components.

Since the frame 12 is molded from a synthetic resin, it will generally exhibit insulating properties, but current can still flow if the voltage is high, such as with static electricity, and therefore static electricity could flow to the blood glucose level sensor 2, the frame 12, the bent piece 29a, the upper face cover 29, the ground connection pieces 29b, and the ground patterns 31a.

Also, in this embodiment the ground patterns 31a are formed integrally with the conductive pattern 31, but the ground patterns 31a and the conductive pattern 31 may instead be formed separately on the connection substrate 30.

Furthermore, in this embodiment, the upper face of the metal upper face cover 29 is a flat surface, and therefore the upper face side of the upper face cover 29 serves as a chucking component for a mounting nozzle (not shown). Therefore, the biological information measurement connector 11 in this embodiment can be checked with a mounting nozzle (not shown), and can be mounted on the connection substrate 30 with a mounting device.

Also, by making the upper face cover 29 of a silver-colored metal, and making the frame 12 of a black synthetic resin, the upper face cover 29 and the frame 12 have different colors and optical reflectivity. Furthermore, as shown in FIG. 3, the upper face of the upper face cover 29 (that is, the mounting nozzle chucking component) is smaller than the upper face of the frame 12, and the upper face of the frame 12 covers the peripheral area around the upper face of the upper face cover 29. Therefore, the silver-colored mounting nozzle chucking component is surrounded by the black frame 12, and when the controller that controls the mounting nozzle determines the location of the mounting nozzle chucking component by means of image processing, for example, it will be easier to recognize the location of the mounting nozzle chucking component.

Also, in this embodiment, as shown in FIG. 5, the conductive pattern 31 is provided on the upper face opposite the lower face opening 12b of the frame 12, on the connection substrate 30 on which the frame 12 is mounted. This conductive pattern 31 is formed by gold plating, for example, and as shown in FIG. 4, in a state before the blood glucose level sensor 2 has been inserted through the sensor insertion port 21, the front end sides of the connection terminals 13 to 20 are all in contact with this conductive pattern 31.

Therefore, in the state in FIG. 4, it can be determined whether or not the connection terminals 13 to 20 are being biased downward. Therefore, if the conductive pattern 31 is connected to a ground line, and if a signal is applied to the rear end side of the connection terminal 13, for example, the signal will flow from the connection terminal 13 to the conductive pattern 31, so this indicates that the connection terminal 13 is being properly biased.

For example, as a biasing determination reference, it can be determined that the connection terminals 13 to 20 are in proper contact with the conductive pattern 31 if the contact resistance is less than 50 mΩ. If the contact resistance is within a range of at least 50 mΩ and less than 1 MΩ, it can be determined that conductive foreign matter has adhered to the connection terminals 13 to 20, or that the contacts have oxidized, etc. and conduction is in an abnormal state. If the contact resistance is at least 1 MΩ, it can be determined that the connection terminals 13 to 20 have broken, or non-conductive foreign matter has adhered, or there is some other open state.

Also, by disposing the conductive pattern 31 in this way, when the rear end of the connection terminal 20 is inserted, conduction will be interrupted for all of the connection terminals 13 to 20, and this reveals that the blood glucose level sensor 2 is properly inserted.

When the blood glucose level sensor 2 is inserted, the static charge of a person can be prevented from affecting the controller 7 and so forth by diverting the flow through the connection terminals 13 to 20 to the controller 7 and so forth to the conductive pattern 31 ahead of time.

Figure 7:
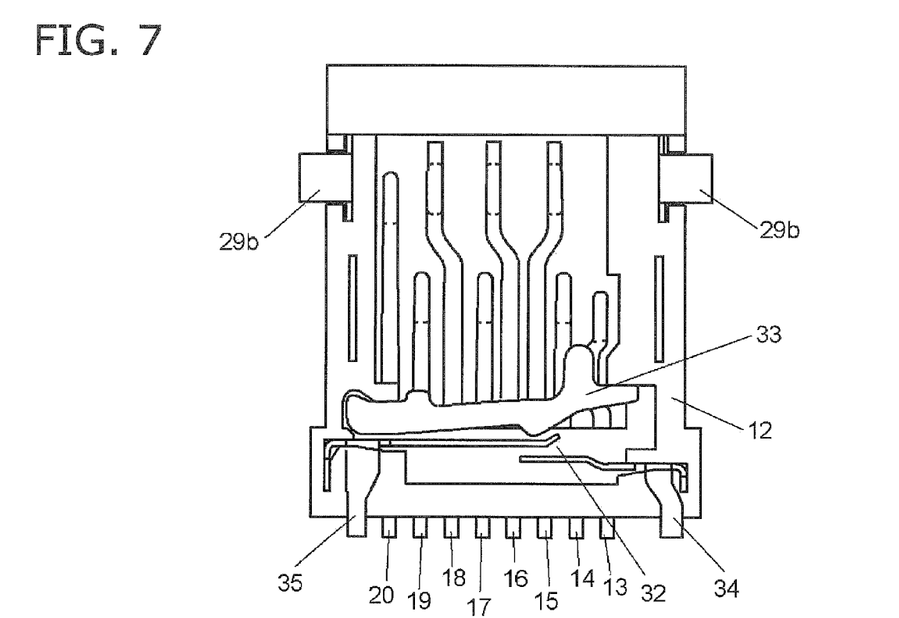
FIG. 7 is a rear view of the connector for biological information measurement in the first embodiment of the present invention.

Also, as shown in FIG. 7, a detector switch 32 that detects the insertion of the blood glucose level sensor 2 is provided on the rear face side of the frame 12, and the proper detection of the blood glucose level sensor 2 is detected by pushing on a control arm 33 disposed ahead of the detector switch 32, with the rear end side of the blood glucose level sensor 2.

An insertion detection terminal 34 and an insertion detection terminal 35 of this detector switch 32 are pulled outside of the frame 12.

As described above, in this embodiment the upper face opening 12a and the lower face opening 12b are provided to the frame 12 of the biological information measurement connector 11 itself, so that the connection terminals 13 to 20 and the sensor insertion port 21 are integrally molded by the upper and lower molds.

With this configuration, in this embodiment the metal upper face cover 29 that covers the entire upper face opening 12a is mounted on the upper face opening 12a of the frame 12. Consequently, no foreign matter will get into the connection terminals 13 to 20 through the upper face opening 12a during storage of the biological information measurement connector 11, or when the biological information measurement connector 11 is mounted on the connection substrate 30 of the biological information measurement device. This prevents connection from being interrupted between the blood glucose level sensor 2 and the connection terminals 13 to 20.

Second Embodiment

Figure 10:
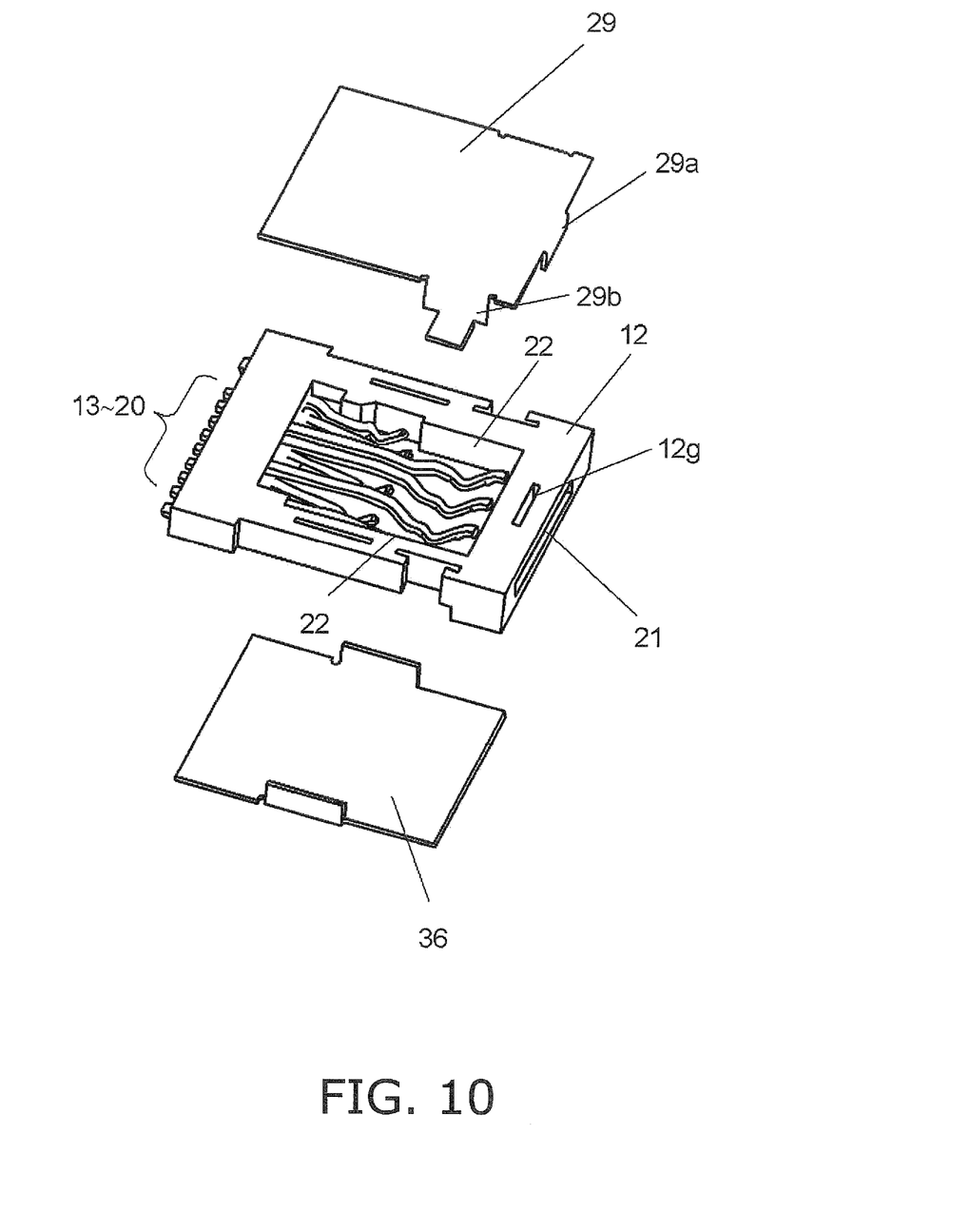
FIG. 10 is an exploded oblique view of the connector for biological information measurement used in the biological information measurement device in a second embodiment of the present invention.

FIG. 10 shows a connector for biological information measurement in a second embodiment of the present invention. Those components that are the same as in the connector for biological information measurement in the first embodiment are numbered the same and will not be described again. In this embodiment, an operation check cover 36 is disposed at the lower face opening 12b of the frame 12. That is, this operation check cover 36 is provided in place of the conductive pattern 31 that was provided to the upper face of the connection substrate 30 in the first embodiment. Accordingly, this operation check cover 36 is made of metal and is connected to a ground line.

With the configuration in this embodiment, the operation of the connector for biological information measurement can be checked by means of a simple configuration.

Again in this embodiment, just as in the first embodiment, the ground connection pieces 29b of the upper face cover 29 are electrically and mechanically connected to the ground patterns 31a so that static electricity will flow to the blood glucose level sensor 2, the frame 12, the bent piece 29a, the upper face cover 29, the ground connection pieces 29b, and the ground patterns 31a.

Third Embodiment

Figure 11:
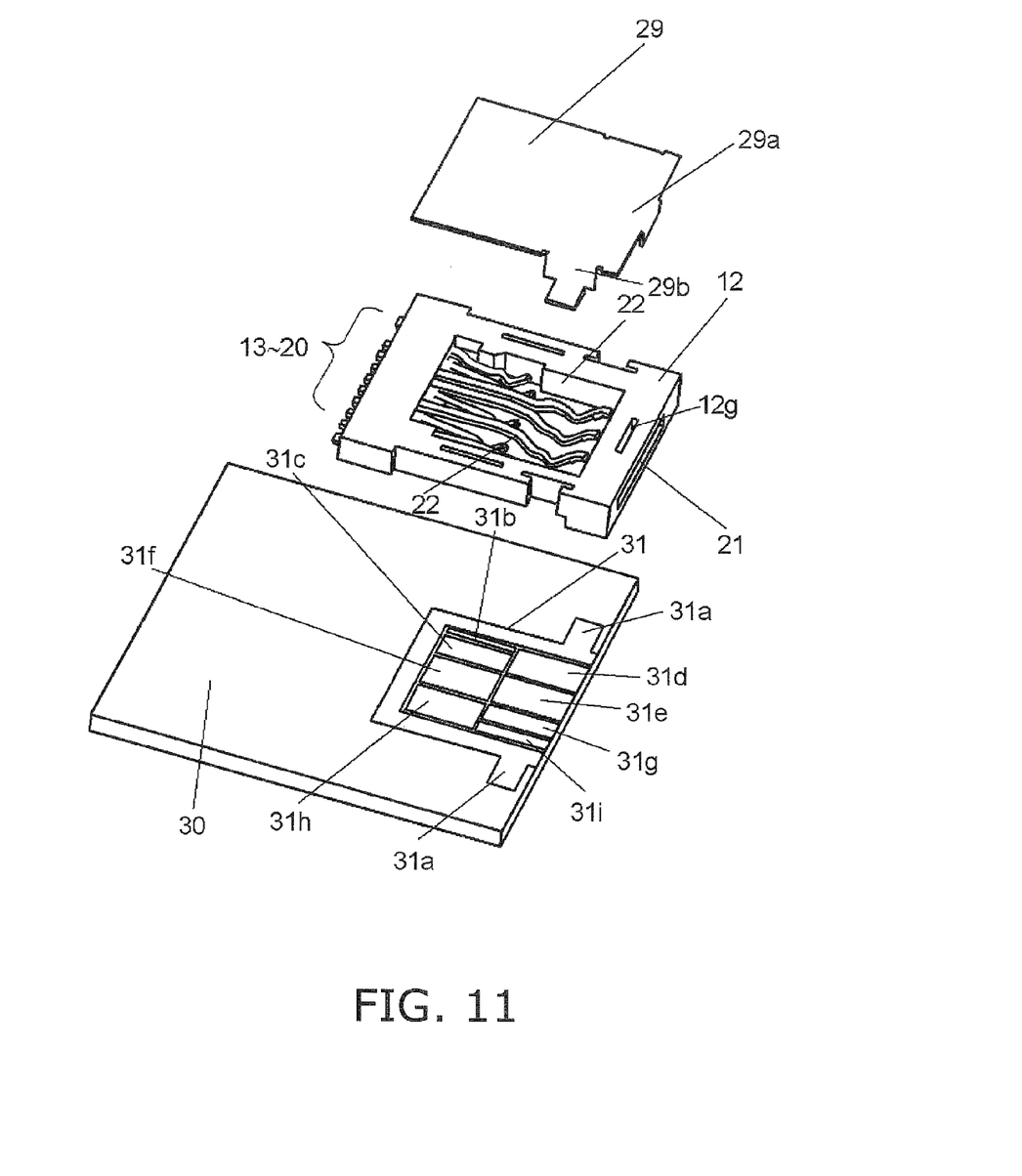
FIG. 11 is an exploded oblique view of the connector for biological information measurement used in the biological information measurement device in a third embodiment of the present invention.

FIG. 11 shows a connector for biological information measurement in a third embodiment of the present invention. Those components that are the same as in the connector for biological information measurement in the first embodiment are numbered the same and will not be described again. In this embodiment, slits are provided to divide up the conductive pattern 31 in FIG. 1, and separate conductive patterns 31b to 31i are disposed in opposition so as to come into individual contact with the terminals of the connection terminals 13 to 20.

Providing these conductive patterns 31b to 31i makes it possible to detect whether or not the various connection terminals are disposed at the proper locations.

For example, the conductive pattern 31b is disposed to come into contact with the connection terminal 13, and the conductive pattern 31c with the connection terminal 14, but if the insertion of the blood glucose level sensor 2, etc., should cause distortion of the connection terminal 13, the connection terminal 13 may come into contact with the conductive pattern 31c instead of the conductive pattern 31b with which it is supposed to come into contact.

If this should happen, the connection terminal 13 will conduct to the conductive pattern 31c instead of the conductive pattern 31b, and this conduction can be detected to detect that the connection terminal 13 is not in the proper location.

Therefore, the fact that the connection terminal 13 is not properly connected to the connection electrode 28 of the blood glucose level sensor 2 can be detected before the blood glucose level sensor 2 is inserted into the biological information measurement connector 11.

Again in this embodiment, just as in the first embodiment, static electricity flows to the blood glucose level sensor 2, the frame 12, the bent piece 29a, the upper face cover 29, the ground connection pieces 29b, and the ground patterns 31a. Therefore, the ground connection pieces 29b of the upper face cover 29 are electrically and mechanically connected to the ground patterns 31a on the outside of the conductive pattern 31d and the conductive pattern 31i.

Fourth Embodiment

Figure 12:
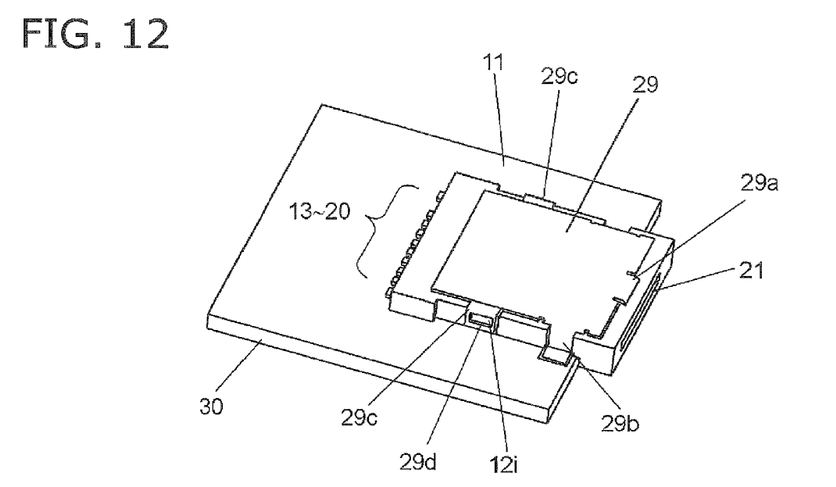
FIG. 12 is an oblique view of the connector for biological information measurement in a fourth embodiment of the present invention.
Figure 13:
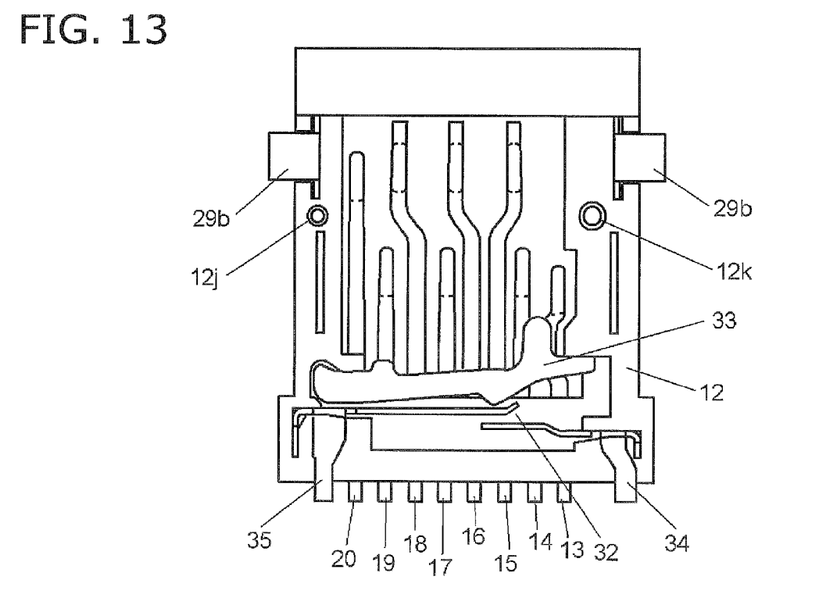
FIG. 13 is a rear view of the connector for biological information measurement in the fourth embodiment of the present invention.
Figure 14:
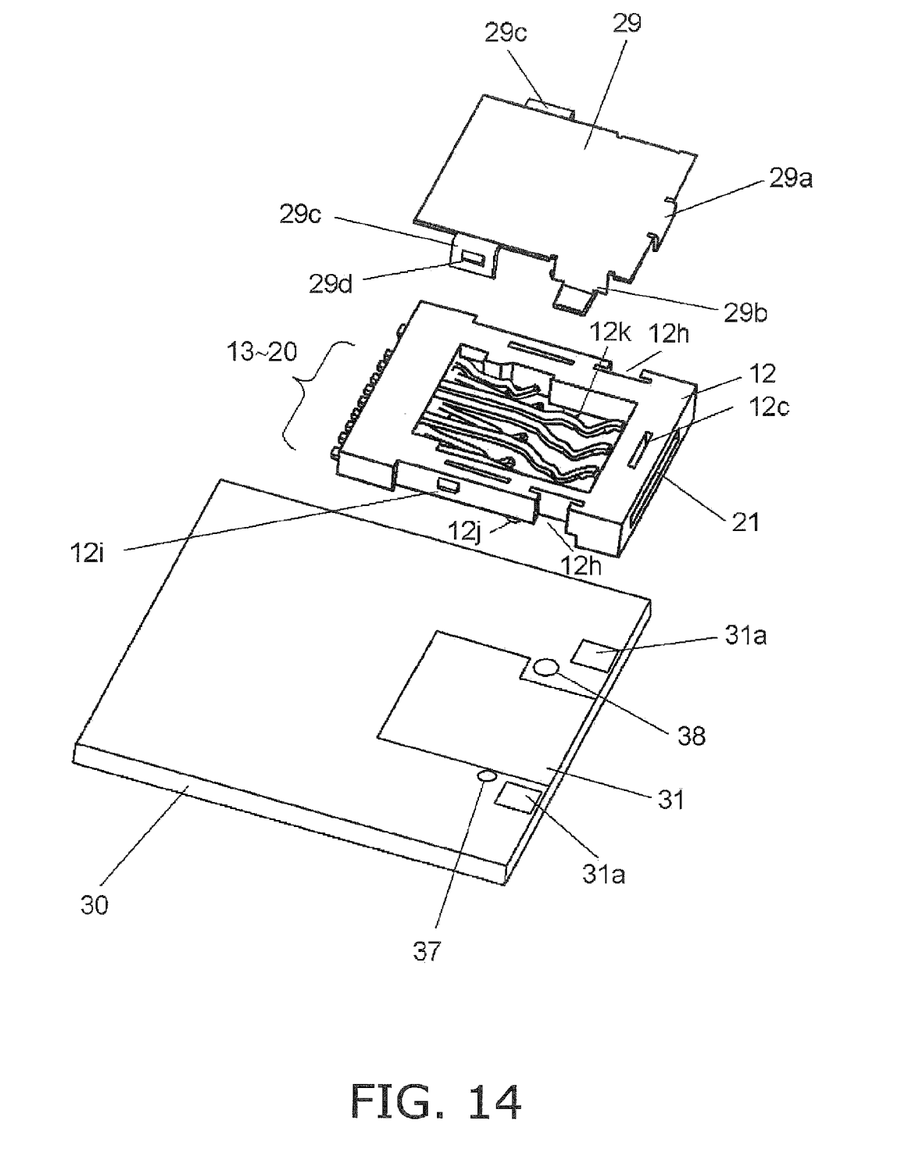
FIG. 14 is an exploded oblique view of the connector for biological information measurement in the fourth embodiment of the present invention.

FIGS. 12 to 14 illustrate a fourth embodiment of the present invention. In this embodiment, latching tabs 29c to the frame 12 are bent downward on the side of the connection terminals 13 to 20 of the upper face cover 29 used in the first embodiment.

That is, the sensor insertion port 21 side of the upper face cover 29 can be integrated by press-fitting the ground connection pieces 29b to latching components 12h (FIG. 14) of the frame 12, but there is the risk that the upper face cover 29 on the side of the connection terminals 13 to 20 will lift up from the frame 12.

In view of this, in this embodiment the latching tabs 29c are provided on the side of the upper face cover 29 with the connection terminals 13 to 20, latching protrusions 12i of the frame 12 protrude into latching holes 29d therein, and this integrates the side of the upper face cover 29 having the connection terminals 13 to 20 with the frame 12.

That is, since the upper face cover 29 is the mounting nozzle chucking surface, this entire upper face cover 29 is preferably integrated with the frame 12, and a way to accomplish this is to provide the ground connection pieces 29b on the sensor insertion port 21 side of the upper face cover 29, and the latching tabs 29c on the side having the connection terminals 13 to 20.

In this embodiment, as shown in FIG. 13, positioning protrusions 12j and 12k are provided on the left and right edges, on the lower face side of the frame 12. Furthermore, as shown in FIG. 14, through-holes 37 and 38 are provided on both sides of the conductive pattern 31 of the connection substrate 30.

That is, in the mounting of the biological information measurement connector 11 on the connection substrate 30 as in FIG. 12, the positioning protrusion 12j of the frame 12 sticks into the through-hole 37 of the connection substrate 30. The positioning protrusion 12k is then stuck into the through-hole 38 of the connection substrate 30, allowing the biological information measurement connector 11 to be mounted at the proper location on the connection substrate 30.

Specifically, the ground connection pieces 29b of the upper face cover 29 are securely brought into contact with the ground patterns 31a, which achieves the above-mentioned goal of dealing with static electricity.

INDUSTRIAL APPLICABILITY

The present invention is expected to find wide application as a connector for biological information measurement, and as a biological information measurement device.

The invention claimed is:

1. A connector for biological information measurement, the connector comprising:
   a square frame molded from resin, the square frame including an upper face opening, a lower face opening, a first edge, and a second edge,
   the first edge disposed between the upper face opening and the lower face opening,
   the second edge disposed between the upper face opening and the lower face opening opposite the first edge, and including a bent piece insertion hole and a sensor insertion port;
   a connection terminal disposed on the first edge of the frame, the connection terminal including a rear end, a middle part, and a front end,
   the rear end extending outside of the frame,
   the middle part embedded in the frame, and
   the front end extending into the frame;
   the sensor insertion port provided between the upper face opening and the lower face opening;
   a metal upper cover mounted on the upper face opening covering the upper face opening, the metal upper cover including a bent piece and a plurality of ground connection pieces;
   the bent piece disposed on a portion of the metal cover nearest the sensor insertion port, and inserted into the bent piece insertion hole; and
   the ground connection pieces formed by extending the outside of the left and right sides of the metal upper cover from the upper face toward the lower face, the ground connection pieces provided in portions of the metal upper cover between the first edge and the second edge of the frame.

2. The connector for biological information measurement according to claim 1, further including:
   a plurality of the connection terminals disposed at a predetermined spacing through the first edge of the frame.

3. The connector for biological information measurement according to claim 1, wherein:
   the square frame further including a left edge and a right edge;

the left edge and the right edge disposed on opposite sides of the square frame between the first edge and the second edge; and each of the left edge and right edge including a sensor insertion guide face between the upper face opening and the lower face opening.

4. The connector for biological information measurement according to claim 1, wherein:

the upper face cover further includes a mounting nozzle chucking component.

5. The connector for biological information measurement according to claim 4, wherein:

a color of the upper face cover is different from a color of the frame.

6. The connector for biological information measurement according to claim 1, wherein:

the lower face opening of the frame further includes an operation check cover.

7. A biological information measurement device, comprising:

a main body case including a sensor mounting component, the sensor mounting component including the connector for biological information measurement device according to claim 1.

8. The biological information measurement device according to claim 7, wherein:

a connection substrate is provided inside of the sensor mounting component, the connector for biological information measurement is disposed on the connection substrate, and a conductive pattern is disposed on the connection substrate opposite the lower face opening of the biological information measurement device.

9. The biological information measurement device according to claim 8, wherein:

the conductive pattern arranged so as to individually come into contact with a plurality of the connection terminals.

10. The biological information measurement device according to claim 7, wherein:

the connection substrate includes a ground pattern configured to contact the ground connection pieces of the upper face cover.

11. A connector for biological information measurement, the connector comprising:

a square frame molded from resin, the square frame including an upper face opening, a lower face opening, a first edge, and a second edge, the first edge disposed between the upper face opening and the lower face opening, the second edge disposed between the upper face opening and the lower face opening opposite the first edge, and including a bent piece insertion hole and a sensor insertion port;

a plurality of connection terminals disposed in the first edge of the frame, each of the connection terminals including a rear end, a middle part, and a front end, the rear end extending outside of the frame, the middle part embedded in the frame, and the front end extending into the frame;

the sensor insertion port provided between the upper face opening and the lower face opening;

a metal upper cover mounted on the upper face opening covering the upper face opening, the metal upper cover including a bent piece and a plurality of ground connection pieces;

the bent piece disposed on a portion of the metal cover nearest the sensor insertion port, and inserted into the bent piece insertion hole; and the ground connection pieces formed by extending the outside of the left and right sides of the metal upper cover from the upper face toward the lower face, the ground connection pieces provided in portions of the metal upper cover between the first edge and the second edge of the frame.

12. The connector for biological information measurement according to claim 11, further including:

the square frame further including a left edge and a right edge;

the left edge and the right edge disposed on opposite sides of the square frame between the first edge and the second edge; and each of the left edge and right edge including a sensor insertion guide face between the upper face opening and the lower face opening.

13. The connector for biological information measurement according to claim 11, wherein:

the upper face cover further includes a mounting nozzle chucking component.

14. The connector for biological information measurement according to claim 13, wherein:

a color of the upper face cover is different from a color of the frame.

15. The connector for biological information measurement according to claim 11, wherein:

the lower face opening of the frame further includes an operation check cover.

16. A biological information measurement device, comprising:

a main body case including a sensor mounting component, the sensor mounting component including the connector for biological information measurement device according to claim 11.

17. The biological information measurement device according to claim 16, wherein:

a connection substrate is provided inside of the sensor mounting component, the connector for biological information measurement is disposed on the connection substrate, and a conductive pattern is disposed on the connection substrate opposite the lower face opening of the biological information measurement device.

18. The biological information measurement device according to claim 17, wherein:

the conductive pattern arranged so as to individually come into contact with a plurality of the connection terminals.

19. The biological information measurement device according to claim 16, wherein:

the connection substrate includes a ground pattern configured to contact the ground connection pieces of the upper face cover.

* * * * *